(12) United States Patent
Kunisada

(10) Patent No.: US 10,655,105 B2
(45) Date of Patent: May 19, 2020

(54) METHOD FOR PROLIFERATION OF PANCREATIC PROGENITOR CELLS

(71) Applicant: Takeda Pharmaceutical Company Limited, Osaka (JP)

(72) Inventor: Yuya Kunisada, Cambridge, MA (US)

(73) Assignee: Takeda Pharmaceutical Company Limited, Fujisawa, Kanagawa (JP)

( * ) Notice: Subject to any disclaimer, the term of this patent is extended or adjusted under 35 U.S.C. 154(b) by 0 days.

(21) Appl. No.: 15/501,703

(22) PCT Filed: Aug. 3, 2015

(86) PCT No.: PCT/JP2015/072591
§ 371 (c)(1),
(2) Date: Feb. 3, 2017

(87) PCT Pub. No.: WO2016/021734
PCT Pub. Date: Feb. 11, 2016

(65) Prior Publication Data
US 2017/0233700 A1 Aug. 17, 2017

(30) Foreign Application Priority Data
Aug. 4, 2014 (JP) .................................. 2014-158470

(51) Int. Cl.
*C12N 5/071* (2010.01)
(52) U.S. Cl.
CPC ......... *C12N 5/0678* (2013.01); *C12N 5/0676* (2013.01); *C12N 2501/11* (2013.01); *C12N 2501/115* (2013.01); *C12N 2501/16* (2013.01); *C12N 2501/385* (2013.01); *C12N 2501/415* (2013.01); *C12N 2501/727* (2013.01); *C12N 2501/998* (2013.01); *C12N 2501/999* (2013.01); *C12N 2506/45* (2013.01); *C12N 2533/52* (2013.01)

(58) Field of Classification Search
None
See application file for complete search history.

(56) References Cited

U.S. PATENT DOCUMENTS

| 2010/0041150 A1 | 2/2010 | Kelly et al. | |
| 2010/0112691 A1* | 5/2010 | Green | C12N 5/0606 435/377 |
| 2013/0022986 A1 | 1/2013 | Hosoya et al. | |
| 2013/0164787 A1* | 6/2013 | Agulnick | C12P 21/00 435/71.1 |

FOREIGN PATENT DOCUMENTS

| JP | 2002-538779 | 11/2002 | |
| JP | 2009-523449 | 6/2009 | |
| JP | 2012-507281 | 3/2012 | |
| WO | WO 2000/47720 | 8/2000 | |
| WO | WO 2007/084730 | 7/2007 | |
| WO | WO 2010/053472 | 5/2010 | |
| WO | WO 2011/081222 | 7/2011 | |
| WO | WO 14/062138 | * 4/2014 | ............... C12N 5/07 |
| WO | WO 2014/124172 | 8/2014 | |

OTHER PUBLICATIONS

Bayramov et al, "Novel functions of Noggin proteins: inhibition of Activin/Nodal and Wnt signaling" Development, Dec. 2011, 138 (24); 5435-56. (Year: 2011).*
Cheng et al.; "Self-Renewing Endodermal Progenitor Lines Generated from Human Pluripotent Stem Cells"; Cell Stem Cell 10, Apr. 6, 2012; pp. 371-384.
Hannan, et al.; "Generation of Multipotent Foregut Stem Cells from Human Pluripotent Stem Cells"; Stem Cell Report; vol. 1; Oct. 15, 2013; pp. 293-306.
Sneddon et al.; "Self-Renewal of Embryonic-Stem-Cell-Derived Progenitors by Organ-Matched Mesenchyme"; Nature; vol. 491, Nov. 29, 2012; pp. 765-770.
Rezania, et al.; "Enrichment of Human Embryonic Stem Cell-Derived NKX6.1—Expressing Pancreatic Progenitor Cells Accelerates the Maturation of Insulin-Secreting Cells in Vivo"; Stem Cells; 2013;31:2432-2442.
Sui et al.; "Role of BMP Signaling in Pancreatic Progenitor Differentiation from Human Embryonic Stem Cells"; Stem Cell Rev and Rep; 2013 9:569-577.
Pagliuca et al.; "Generation of Functional Human Pancreatic B Cells in Vitro"; Cell 159; Oct. 9, 2014; pp. 428-439.
Sui et al.; "FGF Signaling via MAPK is required Early and Improves Activin A-induced Definitive Endoderm Formation from Human Embryonic Stem Cells"; Biochemical and Biophysical Research Communications; 2012; pp. 380-385.
Higuchi et al.; "The Analysis of Wnt Signal in the Differentiation of Pancreatic Progenitor cells in vitro"; Stem Cell Biology; May 15, 2007.
Rezania et al.; "Reversal of Diabetes with Insulin-Producing Cells Derived in vitro from Human Pluripotent Stem Cells"; Nature Biotechnology; vol. 32, No. 11; Nov. 2014.
International Search Report; PCT/JP2015/072591; dated Oct. 27, 2015; 5 pp.
Xu et al.; "Activin, BMP and FGF pathways cooperate to promote endoderm and pancreatic lineage cell differentiation from human embryonic stem cells"; Mech Dev, Sep. 30, 2011, vol. 128, No. 7-10, pp. 412-427.

(Continued)

*Primary Examiner* — Allison M Fox
(74) *Attorney, Agent, or Firm* — Fish & Richardson P.C.

(57) ABSTRACT

The present invention relates to a method for preparing highly pure pancreatic progenitor cells by using pluripotent stem cells such as ES cells or iPS cells as a source, inducing their differentiation into pancreatic progenitor cells, and culturing and proliferating the pancreatic progenitor cells. Specifically, the present invention relates to a method for proliferation of pancreatic progenitor cells, comprising the step of culturing the pancreatic progenitor cells in a medium containing (i) an EGF signal transduction activator and/or an FGF signal transduction activator and (ii) a ROCK inhibitor.

8 Claims, 9 Drawing Sheets

(8 of 9 Drawing Sheet(s) Filed in Color)

(56) References Cited

OTHER PUBLICATIONS

Schulz et al.; "A Scalable System for Production of Functional Pancreatic Progenitors from Human Embryonic Stem Cells"; PLoS One, May 18, 2012, vol. 7, No. 5, pp. e37004.
Liu et al.; "Advances in Experimental Medicine and Biology"; Wnt Signaling in Pancreatic Islets. The Islets of Langerhans, Mar. 10, 2010, pp. 1-797.
Written Opinion; SG Appln. No. 11201700874S; dated Mar. 21, 2018; 9 pages.
Greggio et al., "Artificial three-dimensional niches deconstruct pancreas development in vitro", https://www.ncbi.lm.nih.gov/pmc/articles; Nov. 2013, 11 pages.
Supplementary European Search Report; EP 15 83 0633.2; dated Dec. 22, 2017; 6 pages.
CN Office Action in Chinese Appln. No. 201580047501.8, dated Oct. 23, 2019, 5 pages (English translation).
CN Search Report in Chinese Appln. No. 201580047501.8, dated Oct. 16, 2019, 3 pages (English translation).

* cited by examiner

297L1

(A)

After 1-day passaging  After 4-day passaging (B)

Passage number 5

Passage number 66

METHOD FOR PROLIFERATION OF PANCREATIC PROGENITOR CELLS

RELATED APPLICATION

The present application is a National Phase application under 35 U.S.C. § 371 of International Patent Application No. PCT/JP2015/072591 filed Aug. 3, 2015, which claims priority based on Japanese Patent Application No. 2014-158470, filed on Aug. 4, 2014, the contents of each application are incorporated herein by reference.

TECHNICAL FIELD

The present invention relates to a method for proliferation of pancreatic progenitor cells, and a reagent and a kit for pancreatic progenitor cell proliferation. More specifically, the present invention relates to a method for proliferation of pancreatic progenitor cells, comprising culturing the pancreatic progenitor cells in a medium containing an EGF signal transduction activator and/or an FGF signal transduction activator and a ROCK inhibitor, and a reagent and a kit for the method.

BACKGROUND OF INVENTION

The pancreas has an endocrine gland (endocrine cells) and an exocrine gland (exocrine cells). Pancreatic hormones glucagon, insulin, somatostatin, and pancreatic polypeptide are secreted from pancreatic α cells, pancreatic β cells, pancreatic δ cells, and PP cells, respectively, as endocrine cells, while digestive enzymes such as pancreatic lipase, trypsin, elastase, and pancreatic amylase are secreted from exocrine cells.

Diabetes mellitus is broadly classified into 2 types: type I diabetes mellitus (insulin-dependent diabetes mellitus) and type II diabetes mellitus (insulin-independent diabetes mellitus). Of them, type I diabetes mellitus occurs due to impaired insulin secretion resulting from the destruction of pancreatic β cells producing insulin. A method of regenerating patient-derived pancreatic β cells and transplanting the resulting cells, and a method of transplanting pancreatic β cells differentiation-induced from ES cells or iPS cells as well as a method of attenuating diabetes mellitus by the transplantation of pancreatic progenitor cells is known as treatment methods that have been attempted for type I diabetes mellitus in recent years.

In relation to these treatment methods, there are reports about a method for proliferation of endodermal cells, a method for induction of β cells from the obtained endodermal cells (Patent Literature 1), a method for induction of proliferative endodermal cells from human pluripotent stem cells (Non Patent Literature 1), and a method for induction of proliferative foregut endodermal cells from human pluripotent stem cells (Non Patent Literature 2).

There is also a report about a method for proliferating pancreatic endocrine progenitor cells differentiated from pancreatic progenitor cells (Non Patent Literature 3). These pancreatic endocrine progenitor cells, however, are cocultured with mesenchymal cells. Therefore, the resulting pancreatic endocrine progenitor cells presumably do not have satisfactorily high purity. Furthermore, this report makes no mention about a method for proliferation of pancreatic progenitor cells.

There is a report about a method for induction of NKX6.1-positive pancreatic progenitor cells using human ES cells, and the treatment of diabetes mellitus with highly NKX6.1-expressing pancreatic progenitor cells (Non Patent Literature 4). This report, however, makes no mention about a method for proliferation of pancreatic progenitor cells. Also, it has been reported that insulin-producing cells were differentiation-induced from human ES cells or human iPS cells, transplanted to mice, and studied for their application to the treatment of diabetes mellitus. These reports, however, make no mention about a method for proliferation of pancreatic progenitor cells (Non Patent Literatures 6 and 7).

Pancreatic progenitor cells separated from a living body often halt their proliferation during subculture. Thus, the pancreatic progenitor cells are difficult to efficiently proliferate ex vivo. Sui et al. have reported a method for proliferating ES cell-derived pancreatic progenitor cells using DMEM/F12 medium containing B-27® supplement, FGF10, EGF, and SB431542 (TGFβ inhibitor) (Non Patent Literature 5). This method, however, is still inadequate because the proliferation rate is approximately 30 times in 10 weeks and the obtained pancreatic progenitor cells have purity of approximately 50%.

CITATION LIST

Patent Literature

Patent Literature 1: US2010/0041150

Non Patent Literature

Non Patent Literature 1: Xin Cheng et al., Cell Stem Cell 10 (2012), 371-384
Non Patent Literature 2: Hannan et al., Stem Cell Reports 1 (2013), 293-306
Non Patent Literature 3: Sneddon et al., Nature 491 (2012), 765-770
Non Patent Literature 4: Rezania et al., Stem Cells 31 (2013), 2432-2442
Non Patent Literature 5: Lina Sui et al., Stem Cell Rev and Rep 9 (2013), 569-577
Non Patent Literature 6: Rezania et al. Nature Biotechnology 32 (2014), 1121-1133
Non Patent Literature 7: Pagliuca et al., Cell 159 (2) (2014), 428-439

SUMMARY OF INVENTION

Technical Problem

An object of the present invention is to efficiently proliferate pancreatic progenitor cells ex vivo with their functions maintained. Particularly, an object of the present invention is to provide a method for preparing highly pure pancreatic progenitor cells by using pluripotent stem cells such as ES cells or iPS cells as a source, inducing their differentiation into pancreatic progenitor cells, and culturing and proliferating the pancreatic progenitor cells.

Solution to Problem

The inventors have conducted diligent studies to attain the objects and consequently completed the present invention by finding that highly pure pancreatic progenitor cells are obtained at high efficiency by culturing pancreatic progenitor cells in a medium containing an EGF signal transduction activator and/or an FGF signal transduction activator and a ROCK inhibitor.

Specifically, the present invention relates to the following [1] to [8]:

[1] a method for proliferation of pancreatic progenitor cells (in the present specification, also referred to as the proliferation method of the present invention), comprising subjecting the pancreatic progenitor cells to the following step (1):
(1) culturing the pancreatic progenitor cells in a medium containing (i) an EGF signal transduction activator and/or an FGF signal transduction activator and (ii) a ROCK inhibitor;
[2] the proliferation method according to [1], wherein the medium further contains (iii) a Wnt signal inhibitor;
[3] the proliferation method according to [1] or [2], wherein the pancreatic progenitor cells are pancreatic progenitor cells induced by culturing PDX1-positive cells in a medium containing (a) an EGF signal transduction activator and/or an FGF signal transduction activator and
(b) a Wnt signal inhibitor;
[4] a reagent for proliferation of pancreatic progenitor cells, comprising (i) an EGF signal transduction activator and/or an FGF signal transduction activator and (ii) a ROCK inhibitor;
[5] a kit for proliferation of pancreatic progenitor cells, comprising (i) an EGF signal transduction activator and/or an FGF signal transduction activator and (ii) a ROCK inhibitor;
[6] use of (i) an EGF signal transduction activator and/or an FGF signal transduction activator and (ii) a ROCK inhibitor for proliferating pancreatic progenitor cells;
[7] a method for production of pancreatic progenitor cells, comprising the steps of: culturing and proliferating pancreatic progenitor cells in a medium containing (i) an EGF signal transduction activator and/or an FGF signal transduction activator and (ii) a ROCK inhibitor; and collecting the pancreatic progenitor cells from the cultures; and
[8] the production method according to [7], further comprising the step of culturing PDX1-positive cells in a medium containing (a) an EGF signal transduction activator and/or an FGF signal transduction activator and (b) a Wnt signal inhibitor to induce differentiation thereof into the pancreatic progenitor cells.

In above [1] to [8], the pancreatic progenitor cells and the PDX1-positive cells are preferably human pancreatic progenitor cells and human PDX1-positive cells.

Advantageous Effects of Invention

According to the present invention, pancreatic progenitor cells, which are difficult to proliferate ex vivo, can be prepared at high efficiency and high purity. The method of the present invention can be applied to living body-derived pancreatic progenitor cells as well as pancreatic progenitor cells differentiation-induced from pluripotent stem cells such as ES cells and iPS cells. The obtained pancreatic progenitor cells can be used, either directly or after being induced to differentiate into pancreatic β cells or the like, in the treatment of diabetes mellitus, a testing method for a therapeutic drug for diabetes mellitus, etc.

BRIEF DESCRIPTION OF DRAWINGS

The patent or application file contains at least one drawing executed in color. Copies of the patent or patent application publication with color drawing(s) will be provided by the Office upon request and payment of the necessary fee.

XAV939. NKX6.1-positive cells displayed red color based on Alexa 568. PDX1-positive cells displayed green color based on Alexa 488. The nuclei of cells displayed blue color based on Hoechst 33342. When bFGF, Y27632, and XAV939 were added in combination as well as when Y27632 and bFGF were added in combination and when bFGF and XAV939 were added in combination, the manner in which PDX1-positive and NKX6.1-positive cells were proliferated was observed.

Figure 8:
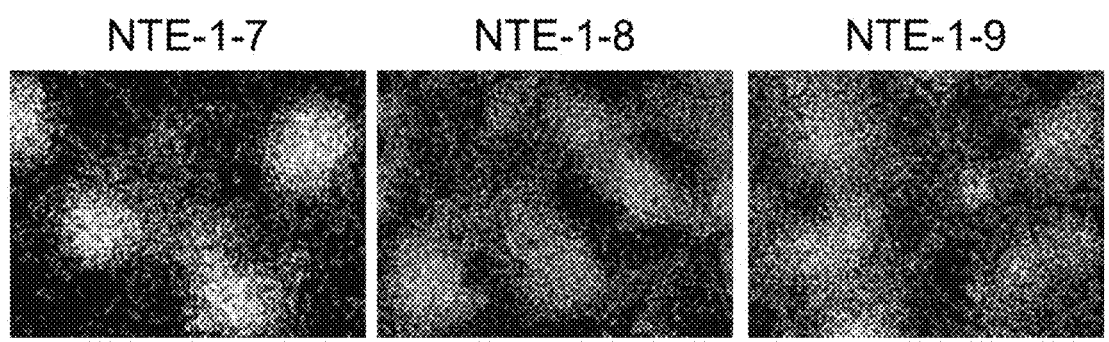

FIG. 8 is staining images of pancreatic progenitor cells induced from each iPS cell line of NTE-1-7 (left), NTE-1-8 (middle), and NTE-1-9 (right) in Example 6. NKX6.1-positive cells displayed red color based on Alexa 568. PDX1-positive cells displayed green color based on Alexa 488. The nuclei of cells displayed blue color based on Hoechst 33342. As is evident, for all of the human iPS cell lines, a great majority of cells were PDX1-positive and NKX6.1-positive by 2 passages of cells differentiation-induced from the iPS cells.

Figure 9:
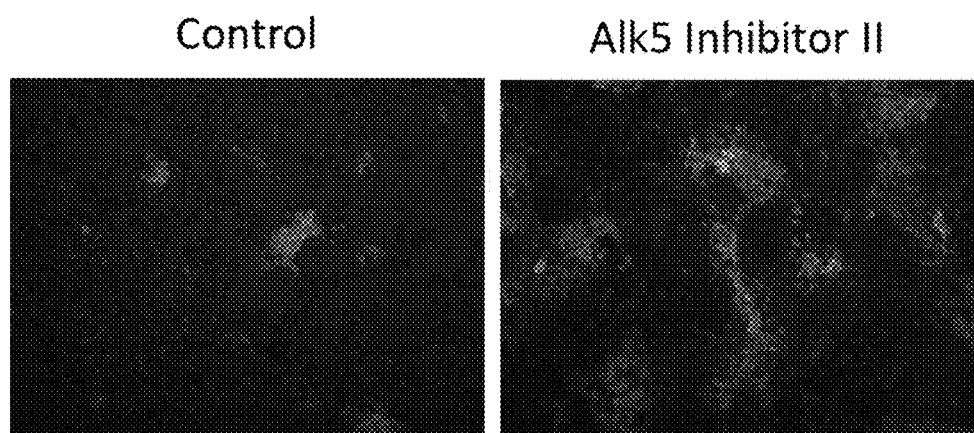

FIG. 9 is staining images of INSULIN-positive cells induced in Reference Example 3. The results shown are about a control (left) and cells cultured using a medium containing Alk5 inhibitor II (right). INSULIN-positive cells displayed red color based on Alexa 568. NKX6.1-positive cells displayed green color based on Alexa 488. The nuclei of cells displayed blue color based on Hoechst 33342. As is evident, INSULIN-positive cells were differentiation-induced from pancreatic progenitor cells by culture using a medium containing the differentiation inducer Alk5 inhibitor II.

DESCRIPTION OF EMBODIMENTS

1. Description of Term

Hereinafter, the terms used in the present invention and the present specification will be described.

The "pancreatic progenitor cells" according to the present invention are endodermal cells that may differentiate into pancreatic endocrine cells and pancreatic exocrine cells, and are characterized by PDX1 positivity, NKX6.1 positivity, and INS (INSULIN) negativity. The "pancreatic progenitor cells" according to the present invention are not particularly limited as long as the pancreatic progenitor cells are mammal-derived. Human pancreatic progenitor cells are preferred.

The pancreatic progenitor cells can be cultured under appropriate conditions and thereby induced to differentiate into "pancreatic β cells (in the present specification, used interchangeably with "insulin-secreting cells")" having the ability to produce insulin. The "pancreatic β cells" are characterized by PDX1 positivity, NKX6.1 positivity, and INS positivity.

The "PDX1-positive cells" according to the present invention are characterized by PDX1 positivity, NKX6.1 negativity, and INS negativity. The "PDX1-positive cells" can be differentiation-induced, for example, from pluripotent stem cells such as ES cells (embryonic stem cells) or iPS cells through endodermal cells. The "endodermal cells" are cells that may differentiate into cells constituting endodermal tissues, and are characterized by positivity to endodermal makers SOX17 and FOXA2. The "PDX1-positive cells" according to the present invention are not particularly limited as long as the PDX1-positive cells are mammal-derived. Human PDX1-positive cells are preferred.

The "pluripotent stem cells" are cells potentially having pluripotent differentiation similar to that of ES cells, i.e., the ability to differentiate into various tissues (all of the endoderm, the mesoderm, and the exoderm) of a living body, and are characterized by positivity to Oct3/4 and Nanog, which are transcriptional factors specifically expressed in pluripotent cells.

Particularly, cells reprogrammed to have pluripotent differentiation similar to that of ES cells, by the introduction of particular factors (nuclear reprogramming factors) to mammalian somatic cells or undifferentiated stem cells are called "induced pluripotent stem cells".

At present, there are various "induced pluripotent stem cells". In addition to iPS cells established for the first time by Yamanaka et al. by introducing 4 factors (Oct3/4, Sox2, Klf4, and c-Myc) to mouse fibroblasts (Takahashi K, Yamanaka S., Cell, (2006), 126: 663-676), human iPS cells established by introducing similar 4 factors to human fibroblasts (Takahashi K, Yamanaka S., et al., Cell, (2007), 131: 861-872.), Nanog-iPS cells established by screening using Nanog expression as an index after introduction of the 4 factors (Okita, K., Ichisaka, T., and Yamanaka, S. (2007), Nature 448, 313-317), and iPS cells prepared by a c-Myc-free method (Nakagawa M, Yamanaka S., et al., Nature Biotechnology, (2008), 26, 101-106) can also be used.

Alternatively, induced pluripotent stem cells prepared by Thomson et al. from University of Wisconsin (Yu J., Thomson JA. et al., Science (2007), 318: 1917-1920.), induced pluripotent stem cells prepared by Daley et al. from Harvard University (Park I H, Daley G Q. et al., Nature (2007), 451: 141-146), induced pluripotent stem cells prepared by Sakurada et al. (Japanese Patent Laid-Open No. 2008-307007), and the like can also be used.

In addition, induced pluripotent stem cells known in the art as described in every published paper (e.g., Shi Y., Ding S., et al., Cell Stem Cell, (2008), Vol. 3, Issue 5, 568-574; Kim J B., Scholer H R., et al., Nature, (2008), 454, 646-650; and Huangfu D., Melton, D A., et al., Nature Biotechnology, (2008), 26, No. 7, 795-797) or patent (e.g., Japanese Patent Laid-Open No. 2008-307007, Japanese Patent Laid-Open No. 2008-283972, US2008-2336610, U52009-047263, WO2007-069666, WO2008-118220, WO2008-124133, WO2008-151058, WO2009-006930, WO2009-006997, and WO2009-007852) can also be used.

The induced pluripotent stem cells can be suitably used as a source for the PDX1-positive cells according to the present invention. The PDX1-positive cells can be obtained by differentiation induction from the induced pluripotent stem cells according to a method described in, for example, WO2011-081222. The "pluripotent stem cells" and the "induced pluripotent stem cells" used in the present invention are not particularly limited as long as these cells are mammal-derived. Human pluripotent stem cells and human induced pluripotent stem cells are preferred.

The cells according to the present invention are characterized by the expression of some markers.

Among these markers, "PDX1 (pancreatic-duodenal homeobox 1)", also known as insulin promoter factor 1, is a transcriptional factor that has an important role in the development of the pancreas and β cell differentiation and also participates in the in vivo functional maintenance of pancreatic β cells. "NKX6.1" is also a transcriptional factor that has an important role in β cell differentiation and also participates in the in vivo functional maintenance of pancreatic β cells, as with PDX1. On the other hand, "INS (INSULIN)" indicates intracellular insulin, and its expression is increased as the differentiation of pancreatic progenitor cells into pancreatic β cells (insulin-producing cells) progresses.

The expression of these markers can be quantitatively detected by immunostaining using antibodies, RT-PCR, etc.

The "EGF signal transduction activator" according to the present invention encompasses every substance that activates a signaling pathway mediated by the EGF (epidermal growth factor) receptor family. Examples thereof can include EGF (particularly, human EGF), functional analogs thereof, TGFα, HB-EGF, Amphiregulin, Betacellulin, and Epiregulin. The EGF signal transduction activator is preferably EGF (particularly, human EGF) or Betacellulin.

The "FGF signal transduction activator" according to the present invention encompasses every substance that activates a signaling pathway mediated by the FGF (fibroblast growth factor) receptor family. Examples thereof can include aFGF (FGF1), bFGF (FGF2), FGF3 to FGF23, and their functional analogs. The FGF signal transduction activator is preferably bFGF, particularly, human bFGF.

The "ROCK inhibitor" according to the present invention means a substance inhibiting Rho kinase (ROCK: Rho-associated, coiled-coil containing protein kinase) and may be a substance inhibiting any of ROCK I and ROCK II. The ROCK inhibitor is not particularly limited as long as the ROCK inhibitor has the function described above. Examples of the ROCK inhibitor that can be used include: N-(4-pyridinyl)-4β-[(R)-1-aminoethyl]cyclohexane-1α-carboxamide (in the present specification, also referred to as Y-27632), Fasudil (HA1077), (2S)-2-methyl-1-[(4-methyl-5-isoquinolinyl)sulfonyl]hexahydro-1H-1,4-diazepine (i.e., H-1152), 4β-[(1R)-1-aminoethyl]-N-(4-pyridyl)benzene-1α-carboxamide (i.e., Wf-536), N-(1H-pyrrolo[2,3-b]pyridin-4-yl)-4PER(R)-1-aminoethyl]cyclohexane-1α-carboxamide (i.e., Y-30141), N-(3-{[2-(4-amino-1,2,5-oxadiazol-3-yl)-1-ethyl-1H-imidazo[4,5-c]pyridin-6-yl]oxy}phenyl)-4-{[2-(4-morpholinyl)ethyl]-oxy}benzamide (i.e., GSK269962A), and N-(6-fluoro-1H-imidazol-5-yl)-6-methyl-2-oxo-4-[4-(trifluoromethyl)phenyl]-3,4-dihydro-1H-pyridine-5-carboxamide (i.e., GSK429286A); antibodies (including functional fragments), antisense nucleic acids, and siRNAs against ROCK; antagonists and dominant negative forms of ROCK; and other ROCK inhibitors known in the art (see e.g., US2005-0209261, US2005-0192304, US2004-0014755, US2004-0002508, US2004-0002507, US2003-0125344, WO2003/082808, US2003-0087919, WO2005/035506, WO2005/074643, WO2004/039796, WO2003/062227, WO2003/062225, WO2003/059913, WO2002/076976, WO2002/076977, WO01/17562, WO00/78351, and WO98/06433). The ROCK inhibitor is preferably N-(4-pyridinyl)-4β-[(R)-1-aminoethyl]cyclohexane-1α-carboxamide (i.e., Y-27632).

The "Wnt signal inhibitor" according to the present invention is a substance inhibiting a Wnt-mediated signaling pathway. Examples thereof include IWP2, IWP3, IWP4, 2-(4-trifluoromethylphenyl)-7,8-dihydro-5H-thiopyrano[4,3-d]pyrimidin-4(3H)-one (in the present specification, also referred to as XAV939), IWR1, G-CSF, IGFBP4, Dkk1, Cerberus, anti-Wnt antibodies, Wnt agonists (Wnt receptor inhibitors), soluble Wnt receptor proteins (Frzb-1, etc.), and dominant negative forms. The Wnt signal inhibitor is preferably 2-(4-trifluoromethylphenyl)-7,8-dihydro-5H-thiopyrano[4,3-d]pyrimidin-4(3H)-one (i.e., XAV939).

2. Method for Proliferation of Pancreatic Progenitor Cells

The method for proliferation of pancreatic progenitor cells according to the present invention comprises culturing the pancreatic progenitor cells in a medium containing (i) an EGF signal transduction activator and/or an FGF signal transduction activator and (ii) a ROCK inhibitor. The step of proliferating pancreatic progenitor cells by this proliferation method is also referred to as a proliferation step in the present specification.

The "medium" for use in the proliferation step is not particularly limited as long as the medium is for use in the culture of stem cells. Examples of the basal medium include BME medium, BGJb medium, CMRL 1066 medium, Glasgow MEM medium, Improved MEM Zinc Option medium, IMDM medium, Medium 199 medium, Eagle MEM medium, αMEM medium, DMEM medium, serum-free DMEM/F12 medium, Ham's medium, RPMI 1640 medium, Fischer's medium, and mixed media thereof. The basal medium is preferably serum-free DMEM/F12 medium, RPMI 1640 medium, or Improved MEM Zinc Option medium, particularly preferably Improved MEM Zinc Option medium.

The medium is preferably a medium substantially free from serum and/or serum extracts, more preferably a serum-free medium. The term "substantially free" means that the content of the serum is less than approximately 1% by volume, preferably less than approximately 0.1% by volume, more preferably less than approximately 0.01% by volume. The "serum-free medium" means a medium containing no unadjusted or unpurified serum. A medium containing a purified blood-derived component or an animal tissue-derived component (e.g., a growth factor) corresponds to the serum-free medium.

The medium may contain a "serum substitute". Examples of the serum substitute include albumins (e.g., lipid-rich albumin), transferrins, fatty acids, collagen precursors, trace elements (e.g., zinc and selenium), B-27® supplement, N2 supplement, Knockout Serum Replacement (manufactured by Invitrogen Corp.), 2-mercaptoethanol, and 3'-thioglycerol. When the serum substitute is B-27® supplement, its concentration in the medium is 0.01 to 10% by weight, preferably 0.1 to 2% by weight.

The medium contains (i) an EGF signal transduction activator and/or an FGF signal transduction activator and (ii) a ROCK inhibitor.

The concentration of the EGF signal transduction activator in the medium is appropriately set according to the type of the substance (factor) used and is usually approximately 0.01 nM to 1000 μM, preferably approximately 0.1 nM to 100 μM. In the case of EGF, its concentration in the medium is approximately 0.005 to 2.0 μg/ml (i.e., approximately 0.8 to 320 nM), preferably approximately 0.005 to 1.0 μg/ml (i.e., approximately 0.8 to 160 nM), more preferably approximately 0.01 to 1.0 μg/ml (i.e., approximately 1.6 to 160 nM).

Examples of the FGF signal transduction activator contained in the medium include the "FGF signal transduction activator" listed above. bFGF (particularly, human bFGF) is preferred. The concentration of the FGF signal transduction activator in the medium is appropriately set according to the type of the substance (factor) used and is usually approximately 0.01 nM to 1000 μM, preferably approximately 0.1 nM to 100 μM. In the case of FGF, its concentration in the medium is approximately 0.005 to 2.0 μg/ml (i.e., approximately 0.3 to 116 nM), preferably approximately 0.005 to 1.0 μg/ml (i.e., approximately 0.3 to 58 nM), more preferably approximately 0.01 to 1.0 μg/ml (i.e., approximately 0.6 to 58 nM). When the EGF signal transduction activator and the FGF signal transduction activator are used in combination, the concentration of each factor is appropriately increased or decreased, for use, on the basis of the concentration range described above.

Examples of the ROCK inhibitor contained in the medium include the "ROCK inhibitor" listed above. N-(4-Pyridinyl)-4β-[(R)-1-aminoethyl]cyclohexane-1α-carboxamide (i.e., Y-27632) is preferred.

The concentration of the ROCK inhibitor in the medium is appropriately set according to the type of the substance (agent) used and is usually approximately 0.01 nM to 1000 μM, preferably approximately 0.1 nM to 100 μM. In the case of Y-27632, its concentration in the medium is approximately 0.1 to 100 μM, preferably approximately 1.0 to 30 μM, more preferably approximately 2.0 to 20 μM.

The medium may further contain a Wnt signal inhibitor.

Examples of the Wnt signal inhibitor contained in the medium include the "Wnt signal inhibitor" listed above. 2-(4-Trifluoromethylphenyl)-7,8-dihydro-5H-thiopyrano[4,3-d]pyrimidin-4(3H)-one (i.e., XAV939) is preferred.

The concentration of the Wnt signal inhibitor in the medium is appropriately set according to the type of the substance (agent) used and is usually approximately 0.01 nM to 1000 μM, preferably approximately 0.1 nM to 100 μM. In the case of XAV939, its concentration in the medium is approximately 0.1 μM or higher, preferably approximately 0.1 to 10 μM, more preferably approximately 0.2 to 5 μM.

The substances (factors or agents) for use in the medium are preferably bFGF (particularly, human bFGF) as the FGF signal transduction activator and N-(4-pyridinyl)-4β-[(R)-1-aminoethyl]cyclohexane-1α-carboxamide (i.e., Y-27632) as the ROCK inhibitor.

The medium may further contain a Wnt signal inhibitor. In this case, the Wnt signal inhibitor is preferably 2-(4-trifluoromethylphenyl)-7,8-dihydro-5H-thiopyrano[4,3-d]pyrimidin-4(3H)-one (i.e., XAV939).

When two or more of these EGF signal transduction activators, FGF signal transduction activators, ROCK inhibitors, or Wnt signal inhibitors are used in combination, the concentration of each factor or inhibitor is appropriately increased or decreased, for use, on the basis of the concentration range described above.

For the cell culture in the proliferation step, it is preferred that the medium should be substantially free from feeder cells and/or feeder cell extracts. The term "substantially free" means that the content of the feeder cells and/or the feeder cell extracts in the medium is less than approximately 5% by volume, preferably less than approximately 1% by volume, more preferably less than approximately 0.01% by volume. This can prevent contamination with foreign matter derived from the feeder cells and circumvent a risk of rejection.

The vessel for use in the proliferation step is not particularly limited as long as the vessel permits culture of pancreatic progenitor cells. Examples of the vessel include flasks, flasks for tissue culture, dishes, petri dishes, dishes for tissue culture, multidishes, microplates, microwell plates, multiplates, multiwell plates, microslides, chamber slides, petri dishes, tubes, trays, culture bags, and roller bottles. In the case of suspension culture, it is preferred that the vessel should be made of a hydrophobic material or should be coated with a material that prevents the adsorption of cells or proteins, such as hydrogel or lipid. For efficiently forming cell aggregates, it is desirable that the vessel should have a U-shaped or V-shaped bottom. On the other hand, in the case of adherent culture, it is desirable that the vessel should have cell adhesiveness, as mentioned later.

In the proliferation method of the present invention, the pancreatic progenitor cells may be induced by adherent culture or suspension culture. In the case of adherent culture, for example, a dish, a flask, a microplate, or a cell culture sheet such as OptiCell® (Nalge Nunc International) is used, and the vessel is preferably surface-treated for improving adhesiveness to cells (hydrophilicity) or coated with a matrix for cell support, such as collagen, gelatin, poly-L-lysine, poly-D-lysine, laminin, or fibronectin. Particularly, type I-collagen, BD Matrigel (Nippon Becton Dickinson Co., Ltd.), fibronectin, vitronectin, or the like is preferably used.

The culture temperature is not particularly limited and may be approximately 30 to 40° C., preferably approximately 37° C. The $CO_2$ concentration may be approximately 1 to 10%, preferably approximately 3 to 8%. The partial pressure of oxygen may be 1 to 10%.

The proliferated cells can be confirmed to be pancreatic progenitor cells by detecting the expression of PDX1 and NKX6.1 mentioned above using immunostaining, etc.

In the proliferation step, the pancreatic progenitor cells can be proliferated even if the ROCK inhibitor in the medium is replaced with the Wnt signal inhibitor.

3. Induction of Pancreatic Progenitor Cells from PDX1-Positive Cells

Pancreatic progenitor cells induced by culturing PDX1-positive cells in a medium containing (a) an EGF signal transduction activator and/or an FGF signal transduction activator and (b) a Wnt signal inhibitor can be used as the pancreatic progenitor cells. The step of inducing pancreatic progenitor cells by culturing PDX1-positive cells in this medium is also referred to as a pancreatic progenitor cell differentiation induction step in the present specification.

The medium for use in the pancreatic progenitor cell differentiation induction step (in the present specification, also referred to as an induction medium) is not particularly limited as long as the medium is for use in the culture of stem cells. Examples of the basal medium include BME medium, BGJb medium, CMRL 1066 medium, Glasgow MEM medium, Improved MEM Zinc Option medium, IMDM medium, Medium 199 medium, Eagle MEM medium, αMEM medium, DMEM medium, serum-free DMEM/F12 medium, Ham's medium, RPMI 1640 medium, Fischer's medium, and mixed media thereof. The basal medium is preferably serum-free DMEM/F12 medium, RPMI 1640 medium, or Improved MEM Zinc Option medium, particularly preferably Improved MEM Zinc Option medium.

The induction medium is preferably a medium substantially free from serum and/or serum extracts, more preferably a serum-free medium. The term "substantially free" means that the content of the serum is less than approximately 1% by volume, preferably less than approximately 0.1% by volume, more preferably less than approximately 0.01% by volume. The "serum-free medium" means a medium containing no unadjusted or unpurified serum. A medium containing a purified blood-derived component or an animal tissue-derived component (e.g., a growth factor) corresponds to the serum-free medium.

The induction medium may contain a "serum substitute". Examples of the serum substitute include albumins (e.g., lipid-rich albumin), transferrins, fatty acids, collagen precursors, trace elements (e.g., zinc and selenium), B-27® supplement, N2 supplement, Knockout Serum Replacement (manufactured by Invitrogen Corp.), 2-mercaptoethanol, and 3'-thioglycerol. When the serum substitute is B-27® supplement, its concentration in the medium is 0.01 to 10% by weight, preferably 0.1 to 2% by weight.

The induction medium contains (a) an EGF signal transduction activator and/or an FGF signal transduction activator and (b) a Wnt signal inhibitor.

Examples of the EGF signal transduction activator in the induction medium include the "EGF signal transduction activator" listed above. EGF (particularly, human EGF) and Betacellulin are preferred.

The concentration of the EGF signal transduction activator in the induction medium is appropriately set according to the type of the substance (factor) used and is usually approximately 0.01 nM to 1000 µM, preferably approximately 0.1 nM to 100 µM. In the case of EGF, its concentration in the induction medium is approximately 0.005 to 2.0 µg/ml (i.e., approximately 0.8 to 320 nM), preferably approximately 0.005 to 1.0 µg/ml (i.e., approximately 0.8 to 160 nM), more preferably approximately 0.01 to 1.0 µg/ml (i.e., approximately 1.6 to 160 nM).

Examples of the FGF signal transduction activator in the induction medium include the "FGF signal transduction activator" listed above. bFGF (particularly, human bFGF) is preferred.

The concentration of the FGF signal transduction activator in the induction medium is appropriately set according to the type of the substance (factor) used and the type of the PDX1-positive cells and is usually approximately 0.01 nM to 1000 µM, preferably approximately 0.1 nM to 100 µM. In the case of FGF, its concentration in the induction medium is approximately 0.005 to 2.0 µg/ml (i.e., approximately 0.3 to 116 nM), preferably approximately 0.005 to 1.0 µg/ml (i.e., approximately 0.3 to 58 nM), more preferably approximately 0.01 to 1.0 µg/ml (i.e., approximately 0.6 to 58 nM). When the EGF signal transduction activator and the FGF signal transduction activator are used in combination, the concentration of each factor is appropriately increased or decreased, for use, on the basis of the concentration range described above.

Examples of the Wnt signal inhibitor in the induction medium include the "Wnt signal inhibitor" listed above. 2-(4-Trifluoromethylphenyl)-7,8-dihydro-5H-thiopyrano[4,3-d]pyrimidin-4(3H)-one (i.e., XAV939) is preferred.

The concentration of the Wnt signal inhibitor in the induction medium is appropriately set according to the type of the substance (agent) used and the type of the PDX1-positive cells and is usually approximately 0.01 nM to 1000 µM, preferably approximately 0.1 nM to 100 µM. In the case of XAV939, its concentration in the induction medium is approximately 0.01 µM or higher, preferably approximately 0.01 to 10 µM, more preferably approximately 0.2 to 5 µM.

The substances (factors or agents) for use in the induction medium are preferably EGF (particularly, human EGF) or Betacellulin as the EGF signal transduction activator and/or bFGF (particularly, human bFGF) as the FGF signal transduction activator, and 2-(4-trifluoromethylphenyl)-7,8-dihydro-5H-thiopyrano[4,3-d]pyrimidin-4(3H)-one (i.e., XAV939) as the Wnt signal inhibitor.

When two or more of these EGF signal transduction activators, FGF signal transduction activators, or Wnt signal inhibitors are used in combination, the concentration of each factor or inhibitor is appropriately increased or decreased, for use, on the basis of the concentration range described above.

For the cell culture in the pancreatic progenitor cell differentiation induction step, it is preferred not to substantially use feeder cells and/or feeder cell extracts, as with the proliferation step. The vessel described in the proliferation step can also be used in this cell culture.

In the pancreatic progenitor cell differentiation induction step, the PDX1-positive cells may be induced by adherent culture or suspension culture. In the case of adherent culture, for example, a dish, a flask, a microplate, or a cell culture sheet such as OptiCell® (Nalge Nunc International) is used, and the vessel is preferably surface-treated for improving adhesiveness to cells (hydrophilicity) or coated with a matrix for cell support, such as collagen, gelatin, poly-L-lysine, poly-D-lysine, laminin, or fibronectin. Particularly, type I-collagen, BD Matrigel (Nippon Becton Dickinson Co., Ltd.), fibronectin, vitronectin, or the like is preferably used.

The culture temperature is not particularly limited and may be approximately 30 to 40° C., preferably approximately 37° C. The $CO_2$ concentration may be approximately 1 to 10%, preferably approximately 3 to 8%. The partial pressure of oxygen may be 1 to 10%.

The differentiation-induced cells can be confirmed to be pancreatic progenitor cells by detecting the expression of PDX1 and NKX6.1 mentioned above using immunostaining, etc.

4. Reagent and Kit for Proliferation of Pancreatic Progenitor Cells

The present invention provides a reagent or a kit for proliferation of pancreatic progenitor cells, comprising (i) an EGF signal transduction activator and/or an FGF signal transduction activator and (ii) a ROCK inhibitor.

The reagent of the present invention may contain the components (i) and (ii) mixed in advance or may contain these components in separate packaged states that permit preparation before use. The reagent of the present invention may further comprise (iii) a Wnt signal inhibitor. If necessary, the reagent of the present invention may also contain an instruction manual.

The kit of the present invention comprises a reagent comprising the components (i) and (ii), as an essential constituent. It is desirable that the kit of the present invention should contain the components (i) and (ii) in separate states that permit preparation before use. Alternatively, the kit of the present invention may contain these components mixed in advance.

The kit of the present invention may further comprise (iii) a Wnt signal inhibitor, in addition to the components (i) and (ii). If necessary, the kit of the present invention may further contain a vessel for culture, a coating agent for the vessel for culture, a medium, components to be added to the medium, other instruments, a reagent for verification of pancreatic progenitor cells (anti-PDX1 antibody, anti-NKX6.1 antibody, etc.), an instruction manual, etc.

The pancreatic progenitor cells that are subject to the reagent and the kit of the present invention may be patient-derived cells or pancreatic progenitor cells regenerated from the patient-derived cells or may be pancreatic progenitor cells induced from pluripotent stem cells such as ES cells or iPS cells.

5. Use for Proliferating Pancreatic Progenitor Cells

The present invention also provides use of (i) an EGF signal transduction activator and/or an FGF signal transduction activator and (ii) a ROCK inhibitor for proliferating pancreatic progenitor cells.

A feature of the use is that the components (i) and (ii) are used in combination for proliferating pancreatic progenitor cells. The use may be combined use of the components (i) and (ii) with a Wnt signal inhibitor. The pancreatic progenitor cells used are not particularly limited and may be patient-derived cells or pancreatic progenitor cells regenerated from the patient-derived cells or may be pancreatic progenitor cells induced from pluripotent stem cells such as ES cells or iPS cells.

6. Method for Production of Pancreatic Progenitor Cells

The present invention provides a method for production of pancreatic progenitor cells, comprising the steps of: culturing and proliferating pancreatic progenitor cells in a medium containing (i) an EGF signal transduction activator and/or an FGF signal transduction activator and (ii) a ROCK inhibitor; and collecting the pancreatic progenitor cells from the cultures.

The pancreatic progenitor cell culture and proliferation step can be carried out according to the description of the paragraph "2. Method for proliferation of pancreatic progenitor cells". Accordingly, the medium may further contain a Wnt signal inhibitor.

The collection (recovery) of the pancreatic progenitor cells from the cultures is carried out according to an ordinary method appropriate for the vessel used in the culture. For example, the pancreatic progenitor cells in the cultures are washed with a buffer such as PBS. Then, an enzyme solution for cell dissociation (trypsin solution, Accutase solution, etc.) is added to the cells and reacted therewith for a given time. After the reaction, a culture solution or the like is added thereto, and then, the culture solution is pipetted several times so that the pancreatic progenitor cells can be dissociated from the culture vessel and recovered.

The production method of the present invention may further comprise, before the proliferation step, the step of culturing PDX1-positive cells in a medium containing (a) an EGF signal transduction activator and/or an FGF signal transduction activator and (b) a Wnt signal inhibitor to induce differentiation thereof into the pancreatic progenitor cells. The differentiation induction of the pancreatic progenitor cells from the PDX1-positive cells can be carried out according to the description of the paragraph "3. Method for induction of pancreatic progenitor cells from PDX1-positive cells".

7. Utilization of Pancreatic Progenitor Cells

The pancreatic progenitor cells obtained by the proliferation method or the production method of the present invention have high proliferative capacity, also retain functions, and are highly pure. In addition, highly safe pancreatic progenitor cells containing no impurities are obtained by culture using a medium substantially free from serum and serum extracts without coculture with feeder cells or other cells.

When the pancreatic progenitor cells of the present invention are cells induced from induced pluripotent stem cells prepared by an approach involving gene insertion into the genome, the pancreatic progenitor cells are discriminated from natural pancreatic progenitor cells because of retaining nuclear reprogramming factors derived from the induced pluripotent stem cells, but do not differ in functions from the natural pancreatic progenitor cells.

From the properties as described above, the pancreatic progenitor cells obtained by the method of the present invention are useful in the cell therapy of diabetes mellitus. For example, the pancreatic progenitor cells can be administered to a diabetes mellitus patient to thereby attenuate the diabetes mellitus (Stem Cells. 2013 November; 31 (11): 2432-42).

Furthermore, the pancreatic progenitor cells prepared by the method of the present invention can be induced to differentiate into INS-positive insulin-producing cells (pancreatic β cells) by use of a method conventionally known in the art (Stem Cell Research 2012, 8, 274-284). The obtained pancreatic β cells can be administered to a diabetes mellitus patient to thereby treat the diabetes mellitus. A medicament (cell preparation for treatment of diabetes mellitus) containing the pancreatic progenitor cells of the present invention or such pancreatic β cells induced from the pancreatic progenitor cells of the present invention is also included in the scope of the present invention.

Moreover, the pancreatic progenitor cells obtained by the method of the present invention or the pancreatic β cells induced from the pancreatic progenitor cells retain functions similar to those of in vivo cells and as such, are also useful in a screening or evaluation system for a therapeutic drug for diabetes mellitus.

For example, the pancreatic progenitor cells of the present invention or the pancreatic β cells induced from the pancreatic progenitor cells are cultured in the presence and absence of a test compound. The expression level of insulin or mRNA thereof in the cells or the amount of insulin secreted to the outside of the cells is measured. When the expression level or the amount of insulin secreted in the presence of the test compound is significantly increased as compared with that in the absence of the test compound, the test compound can be selected (screened for) as a therapeutic drug candidate for diabetes mellitus. Such a screening method or an evaluation system is also included in the scope of the present invention.

Another example of the screening includes a method of placing the pancreatic β cells induced from the pancreatic progenitor cells of the present invention under stress that mimics a diabetes mellitus condition, and evaluating a test compound for its effect on the state of reduced functions as the β cells. In this case, when the functions of the β cells are restored or when marker expression associated with the restoration of the functions of the β cells is varied, the test compound can be selected (screened for) as a therapeutic drug candidate for diabetes mellitus. Such a screening method or an evaluation system is also included in the scope of the present invention.

EXAMPLES

Hereinafter, the present invention will be specifically described with reference to Reference Examples and Examples. However, the present invention is not intended to be limited by these Examples.

(Reference Example 1) Induction of PDX1-Positive Cells in Human iPS Cell Line 253G1 Cells 253G1 cells (iPS cell line prepared by the expression of OCT4, SOX2, and KLF4 using retrovirus; Nature Biotechnology 26, 101-106) were used as human iPS cells.

The human iPS cells were cultured using Essential 8 medium (Life Technologies Corp.) in a 6-cm dish or a 10-cm dish coated with vitronectin (Life Technologies Corp.) (in the present specification, also referred to as a vitronectin-coated dish). For passaging, the human iPS cells were dispersed into the state of small cell masses by treatment with 0.5 mM EDTA/PBS and inoculated to a vitronectin-coated dish. The passage ratio was 1:5 to 1:100 depending on the state of the cells, and Essential 8 medium supplemented with 10 μM Y27632 (Wako Pure Chemical Industries, Ltd.) was used only immediately after a passage. On culture day 2 or later, Essential 8 medium alone was used and replaced with a fresh one every day, and the passaging was carried out every 3 to 7 days.

For differentiation induction, first, the undifferentiated iPS cells were inoculated to a 96-well plate. The iPS cells maintained in the state of cell masses were treated with an EDTA solution and thereby dissociated until becoming single cells. Subsequently, the iPS cells dispersed in a medium were inoculated at a density of $2\times10^4$ cells/well to a 96-well plate coated with Matrigel, and cultured at 37° C. under 5% $CO_2$. The culture solution used in the inoculation was Essential 8 medium supplemented with 10 µM Y27632. One day after the inoculation, the medium was replaced with Essential 8 alone, and the cells were further cultured for 1 day until confluent.

Next, the differentiation of the iPS cells into endodermal cells was induced. First, the confluent cells were washed with RPMI medium (Life Technologies Corp.). Then, RPMI medium containing activin A (100 ng/ml) (PeproTech, Inc.), a GSK3β inhibitor CHIR99021 (3 µM) (Axon), and 1% insulin-free B-27® (Life Technologies Corp.) was added to the cells, which were then cultured for 4 days.

Next, the differentiation of the endodermal cells into PDX1-positive cells was induced. The endodermal cells thus differentiation-induced from the iPS cells were washed with Improved MEM Zinc Option medium (Life Technologies Corp.) (in the present specification, also referred to as IMEM-option $Zn^{++}$ medium), which was then replaced with IMEM-option $Zn^{++}$ medium (containing 1% B-27®) supplemented with dorsomorphin (1 µM) (Calbiochem), retinoic acid (2 µM) (Sigma-Aldrich Co. LLC), and SB431542 (10 µM) (Wako Pure Chemical Industries, Ltd.). On day 3 or 4 after the replacement, the medium was replaced with the same medium as above. The differentiation induction of the PDX1-positive cells from the endodermal cells was carried out for a total of 7 days.

(Example 1) Induction of Pancreatic Progenitor Cells Using PDX1-Positive Cells—1

The PDX1-positive cells differentiation-induced on a Matrigel-coated dish according to Reference Example 1 were washed with IMEM-option $Zn^{++}$ medium and then further cultured for 7 days in IMEM-option $Zn^{++}$ medium (containing 1% B-27®) supplemented with XAV939 (1 µM) and/or bFGF (100 ng/ml) (PeproTech, Inc.).

In order to examine the expression of PDX1 and NKX6.1 proteins in the cells thus cultured, immunofluorescence staining was carried out using an anti-PDX1 antibody and an anti-NKX6.1 antibody. Specifically, to the cultured cells, 4% paraformaldehyde in a phosphate buffer solution (4% PFA) (Wako Pure Chemical Industries, Ltd.) was added, and the cells were fixed therewith at room temperature for 30 minutes. Then, the cells were reacted with an anti-PDX1 antibody (AF2419, R&D Systems, Inc.) and an anti-NKX6.1 antibody (55F55A12-c, Developmental Studies Hybridoma Bank) as primary antibodies and further with an Alexa 488-labeled secondary antibody or an Alexa 568-labeled secondary antibody (both from Life Technologies Corp.) as a secondary antibody, sequentially, and then observed under a fluorescence microscope. The results are shown in FIG. 1.

Figure 1:
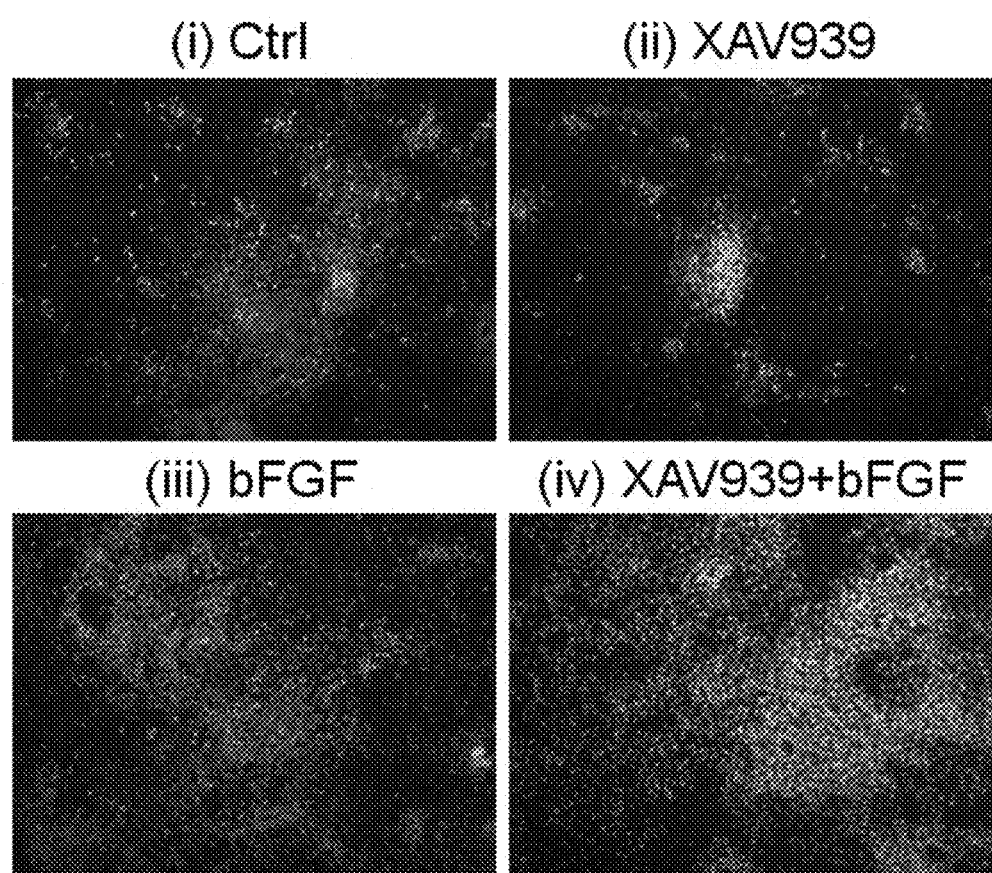
FIG. 1 is staining images of pancreatic progenitor cells induced in Example 1. The results shown are about (i) a control and the addition of (ii) XAV939, (iii) bFGF, and (iv) XAV939+bFGF. NKX6.1-positive cells displayed red color based on Alexa 568. PDX1-positive cells displayed green color based on Alexa 488. The nuclei of cells displayed blue color based on Hoechst 33342. When XAV939 and bFGF were added in combination, the highest proportion of PDX1-positive and NKX6.1-positive cells was obtained.

When XAV939 and bFGF were added as differentiation inducers in combination (FIG. 1(*iv*)), the manner in which a great majority of cells expressed PDX1 and NKX6.1 was observed. On the other hand, when XAV939 was added alone (FIG. 1(*ii*)) or when bFGF was added alone (FIG. 1(*iii*)), cells coexpressing PDX1 and NKX6.1 were few in number.

These results of the study demonstrated that pancreatic progenitor cells can be efficiently induced by culture in a medium supplemented with XAV939 and bFGF.

(Example 2) Induction of Pancreatic Progenitor Cells Using PDX1-Positive Cells—2

The PDX1-positive cells differentiation-induced on a Matrigel-coated dish according to Reference Example 1 were washed with IMEM-option $Zn^{++}$ medium. Then, the medium was replaced with IMEM-option $Zn^{++}$ medium (containing 1% B-27® and 1 µM XAV939) supplemented with EGF (500 ng/ml), Betacellulin (40 ng/ml), or bFGF (100 ng/ml), and the cells were cultured for 8 days. The cells thus cultured were subjected to the immunofluorescence staining described in Example 1 and observed under a fluorescence microscope. The results are shown in FIG. 2.

Figure 2:
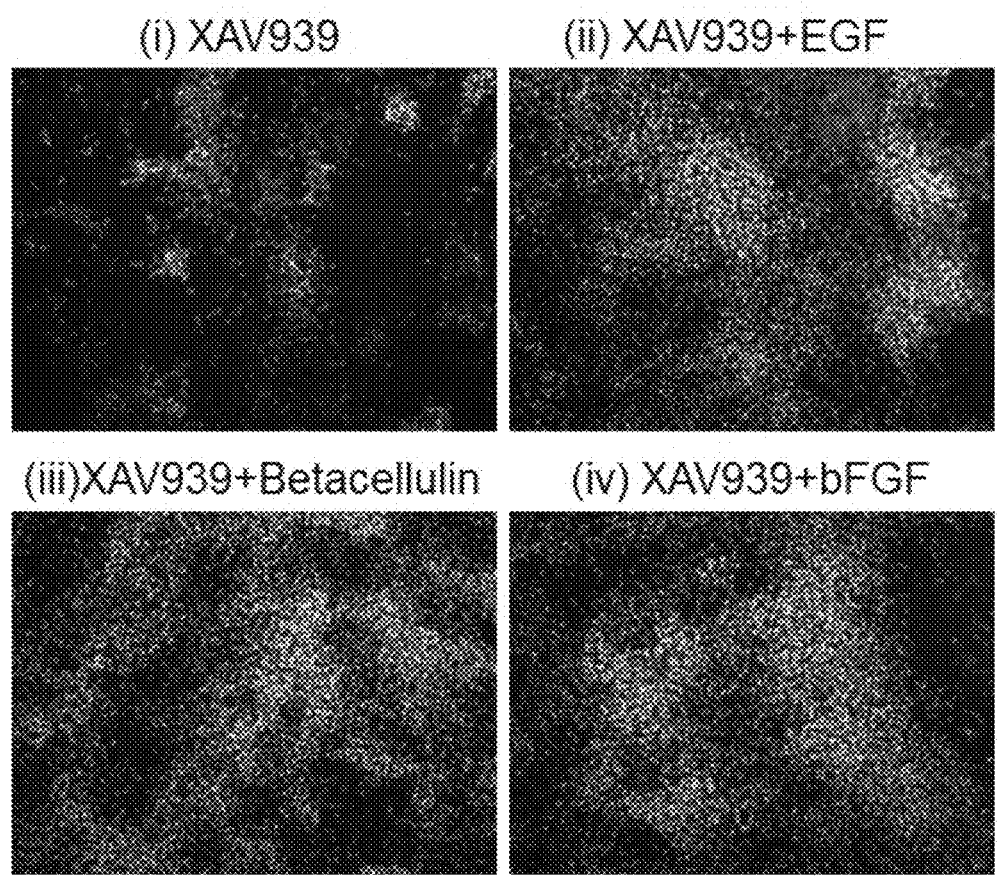
FIG. 2 is staining images of pancreatic progenitor cells induced in Example 2. The results shown are about the addition of (i) XAV939, (ii) XAV939+EGF, (iii) XAV939+Betacellulin, and (iv) XAV939+bFGF. NKX6.1-positive cells displayed red color based on Alexa 568. PDX1-positive cells displayed green color based on Alexa 488. The nuclei of cells displayed blue color based on Hoechst 33342. When bFGF and XAV939 were added in combination as well as when EGF and XAV939 were added in combination and when Betacellulin and XAV939 were added in combination, a high proportion of PDX1-positive and NKX6.1-positive cells was obtained.

As with the case of adding bFGF and XAV939 in combination (FIG. 2(*iv*)), when EGF and XAV939 (FIG. 2(*ii*)) or Betacellulin and XAV939 (FIG. 2(*iii*)) were added in combination, many pancreatic progenitor cells were also induced.

These results demonstrated that pancreatic progenitor cells can be efficiently induced by using a medium supplemented with the EGF signal activation promoter or the FGF signal activation promoter and the Wnt signal inhibitor such as XAV939.

Figure 3:
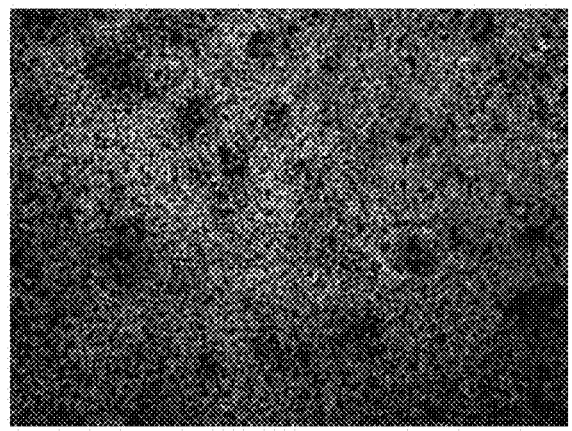
FIG. 3 is a staining image of pancreatic progenitor cells induced from 297L cells in Example 3. NKX6.1-positive cells displayed red color based on Alexa 568. PDX1-positive cells displayed green color based on Alexa 488. The nuclei of cells displayed blue color based on Hoechst 33342. In the case of using the 297L1 cell line, a great majority of cells were also able to be induced into PDX1-positive and NKX6.1-positive cells by the addition of XAV939 and bFGF in combination.

(Example 3) Induction of Pancreatic Progenitor Cells Using Human iPS Cell Line 297L1 Cells PDX1-positive cells were induced according to Reference Example 1 using 297L1 cells (NHDF-iPS; human iPS cell line prepared by the expression of OCT4, SOX2, KLF4, and c-MYC in dermal fibroblasts of a newborn male) (see PLoS ONE 2009; 4 (12), p. e8067). The PDX1-positive cells were washed with IMEM-option $Zn^{++}$ medium and then further cultured for 7 days using IMEM-option $Zn^{++}$ medium (containing 1% B-27®) supplemented with XAV939 (1 µM) and bFGF (50 ng/ml). The cells thus cultured were subjected to the immunofluorescence staining described in Example 1 and observed under a fluorescence microscope. The results are shown in FIG. 3.

In the case of using 297L1 cells, it was also confirmed that pancreatic progenitor cells can be efficiently induced according to the methods described in Reference Example 1, Example 1, and Example 2.

(Example 4) Passaging of Pancreatic Progenitor Cells

The pancreatic progenitor cells induced in Example 3 were passaged by the following procedures: after washing with PBS, Accutase (Innovative Cell Technologies, Inc.) was added to the cells, which were then incubated for 4 minutes and further brought to a single cell state by pipetting. The cells were washed with IMEM-option $Zn^{++}$ medium and then inoculated to a fresh culture vessel at ¼ to ¹⁄₁₀ of the cell concentration before passaging. The medium used was IMEM-option $Zn^{++}$ medium (containing 1% B-27®) supplemented with Y27632 (10 µM), XAV939 (1 µM), and bFGF (50 ng/ml), and the culture vessel used was coated with Matrigel. After the inoculation, the medium was replaced with a fresh one every day.

Figure 4:
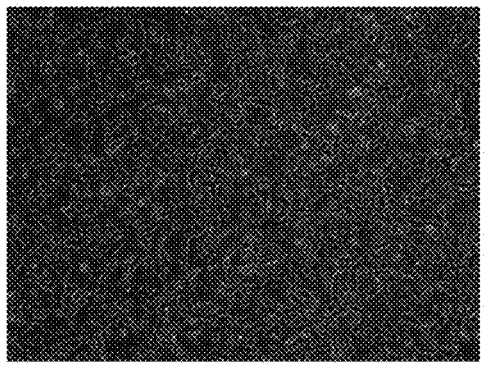
FIG. 4(A) shows photographs of cells taken after 1-day passaging (left) and after 4-day passaging (right). Pancreatic progenitor cells (297L1-derived, passage number: 4) were dissociated from a culture vessel, and then, a portion of the cells was passaged to another culture vessel and cultured. The cell density was low on culture day 1, but was elevated on culture day 4.
FIG. 4(B) shows the relationship between passage numbers and the amount of cells. After proliferation of pancreatic progenitor cells, a portion of the cells was passaged and proliferated again. This operation was continued 21 times. The amount of cells at the time of each passage was measured to thereby calculate what number of cells one cell was proliferated into with increase in passage number. It was shown that the cells were proliferated at a stable speed and proliferated at a speed where one cell was increased to $1 \times 10^{18}$ cells by 21 passages.
Figure 4:
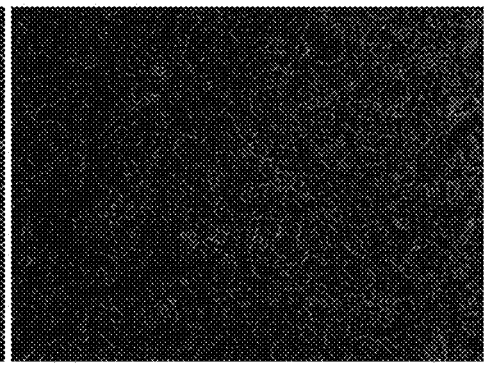
Figure 4:
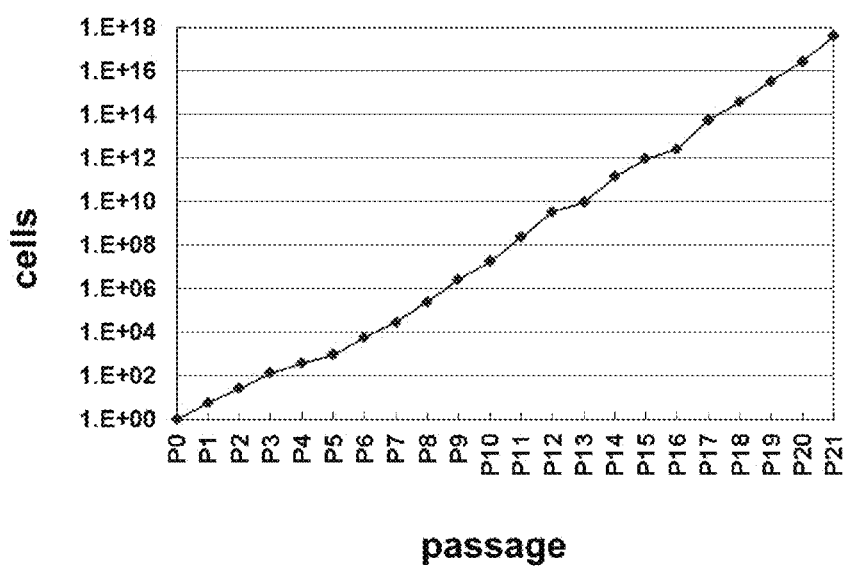

3 to 6 days after the inoculation, the cells reached 80 to 90% confluence. At the stage where the cells reached 80 to 90% confluence, the procedures described above were repeated again for passaging. The appearance of the cells on passaging day 1 and the appearance of the cells on passaging day 4 at a passage number of 4 are shown in FIG. 4A. As is evident, the cell density was low on passaging day 1, but was elevated on passaging day 4. As a result of repeating the passaging in this way, one cell was found to be proliferated into $1\times10^{18}$ cells through 21 passages (FIG. 4B).

These results revealed that pancreatic progenitor cells maintained high proliferative ability even if the passage number exceeds 20.

Figure 5:
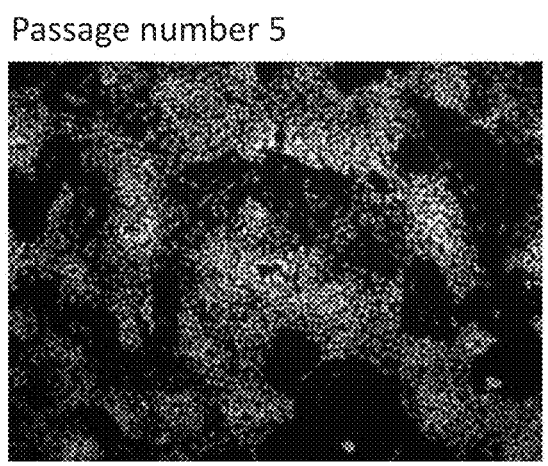
FIG. 5 Immunofluorescence staining using an anti-PDX1 antibody and an anti-NKX6.1 antibody was carried out for pancreatic progenitor cells passaged 5 times (left) and pancreatic progenitor cells passaged 66 times (right). NKX6.1-positive cells displayed red color based on Alexa 568. PDX1-positive cells displayed green color based on Alexa 488. The nuclei of cells displayed blue color based on Hoechst 33342. As is evident, both for the cells passaged 5 times and for the cells passaged 66 times, a great majority of cells were PDX1-positive and NKX6.1-positive.
Figure 5:
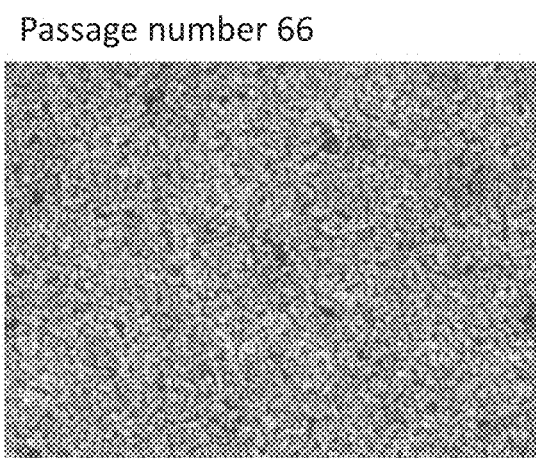

In order to observe the maintenance of the expression of PDX1 and NKX6.1 in the cells with increase in passage number, cells with a passage number of 5 or a passage number of 66 were subjected to the immunofluorescence staining described in Example 1 and observed under a fluorescence microscope. The results are shown in FIG. 5.

Both for the cells with a passage number of 5 and for the cells with a passage number of 66, a great majority of cells were PDX1-positive and NKX6.1-positive.

The results described above demonstrated that PDX1-positive and NKX6.1-positive pancreatic progenitor cells can be proliferated in this state and further passaged by use of the method of the present invention.

(Reference Example 2) Karyotyping of Proliferated Pancreatic Progenitor Cells

Figure 6:
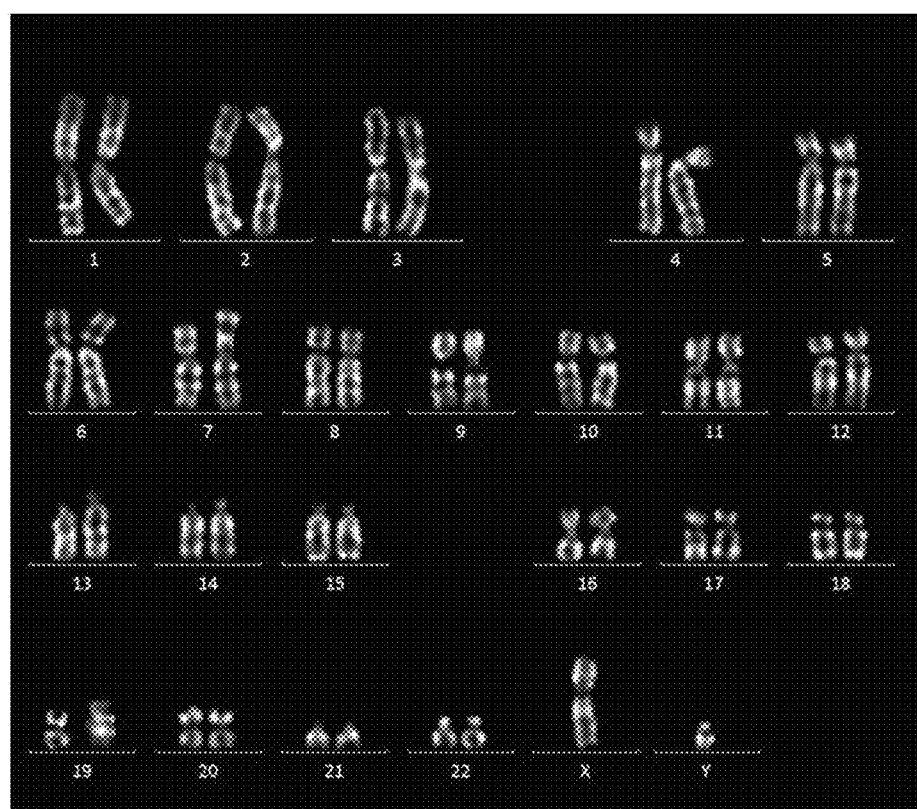
FIG. 6 shows results of conducting Q-band karyotyping after 28 repetitive passages and subsequent fixation of pancreatic progenitor cells with a Carnoy fluid. As is evident, the cells normally carried all of the chromosomes.

The proliferated pancreatic progenitor cells were analyzed for whether to retain normal karyotype with increase in passage number. The pancreatic progenitor cells passaged 28 times were fixed with a Carnoy fluid and then subjected to simple karyotyping (Q-Band) (Chromocenter Inc.). The results are shown in FIG. 6. The results demonstrated that the pancreatic progenitor cells retain normal karyotype and maintain the normal karyotype even after passages by long-term culture.

(Example 5) Involvement in Added Factors in Proliferation of Pancreatic Progenitor Cells As shown in Example 4, the pancreatic progenitor cells were able to be stably proliferated by culture using a medium supplemented with Y27632, XAV939, and bFGF. Accordingly, among these factors, a combination of factors necessary for proliferation of pancreatic progenitor cells was studied.

The pancreatic progenitor cells with a passage number of 44 brought to a single cell state were inoculated to a plate coated with Matrigel, and cultured for 2 days in IMEM-option $Zn^{++}$ medium (containing 1% B-27®) supplemented with each combination of the factors or agents (bFGF (50 ng/ml), XAV939 (1 μM), and Y27632 (10 μM)). After the start of the culture, the medium was replaced with a fresh one every day. The cells thus cultured were subjected to the immunofluorescence staining described in Example 1 and observed under a fluorescence microscope. The results are shown in FIG. 7.

Figure 7:
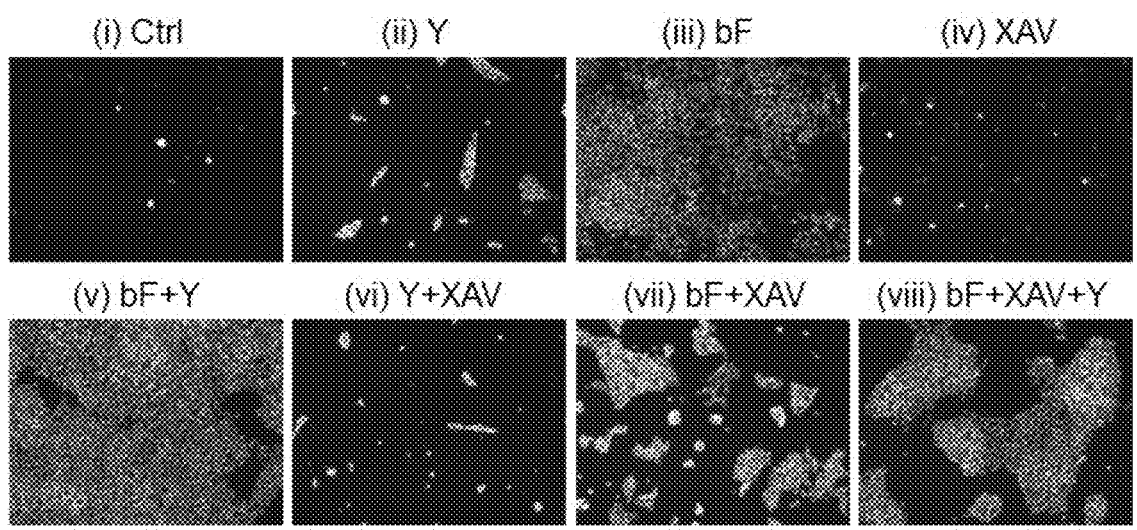
FIG. 7 shows results of bringing pancreatic progenitor cells with a passage number of 44 to a single cell state, then inoculating the cells into a culture solution containing factors shown in the drawing, and culturing the cells for 2 days, followed by immunofluorescence staining using an anti-PDX1 antibody and an anti-NKX6.1 antibody. The results shown are about (i) a control and addition of (ii) Y27632, (iii) bFGF, (iv) XAV939, (v) bFGF+Y27632, (vi) Y27632+XAV939, (vii) bFGF+XAV939, and (viii) bFGF+Y27632+

When bFGF, XAV939, and Y27632 were added in combination (FIG. 7(viii)) as well as when Y27632 and bFGF were added in combination (FIG. 7(v)) and when bFGF and XAV939 were added in combination (FIG. 7(vii)), the manner in which PDX1-positive and NKX6.1-positive cells were proliferated was observed.

(Example 6) Induction of Pancreatic Progenitor Cells Capable of Proliferating Using Other Human iPS Cell Lines Study was made on whether or not pancreatic progenitor cells capable of proliferating could also be induced from other human iPS cells. First, new human iPS cells were prepared by the following method: blood collected into a heparin sodium-containing blood collection tube (Terumo Corp.) was diluted 2-fold with PBS, then layered on Ficoll-Paque PREMIUM (GE Healthcare Japan Corp.), and centrifuged at 400 g at 20° C. for 30 minutes to separate peripheral blood mononucleated cells (PBMCs). Ficoll and the diluted blood were used at a ratio of 3:4. The recovered PBMCs were washed by centrifugation using PBS and then resuspended in StemSpan H3000 (STEMCELL Technologies Inc.). Alternatively, the PBMCs were cryopreserved using Cell Banker 3 (Nippon Zenyaku Kogyo Co., Ltd.). Next, the PBMCs were inoculated at a concentration of $3\times10^6$ cells/well to a 6-well plate. 10 ng/ml IL-3 (PeproTech, Inc.), 100 ng/ml IL-6 (PeproTech, Inc.), 300 ng/ml SCF (PeproTech, Inc.), 300 ng/ml TPO (PeproTech, Inc.), and 300 ng/ml Fit3 ligand (PeproTech, Inc.) were added (hereinafter, referred to as a medium for non-T cells) to the cells, which were then cultured for 6 days. After the culture, the proliferated non-T cells were recovered (approximately $1.3\times10^6$ cells/well) and transfected with episomal vectors included in Plasmids Epi5™ Episomal iPSC Reprogramming Kit (Life Technologies Corp.) using Human CD34 Cell Nucleofector® Kit (Lonza Group Ltd.). As for the amount of the vectors, 1.5 μg each (a total of 3 μg) of Epi5™ Reprogramming Vectors and Epi5™ p53 & EBNA Vectors in the Reprogramming kit was used per $1.3\times10^6$ cells, and U-008 was used as the transfection program of Nucleofector (Lonza Group Ltd.). The cells thus transfected were resuspended in a medium for non-T cells, inoculated to a 10-cm dish (amount of a medium: 10 ml) coated with Geltrex (Life Technologies Corp.), and cultured for 24 hours. On the next day (day 1), DMEM/F12 (Wako Pure Chemical Industries, Ltd.) medium containing 1% N2 (Wako Pure Chemical Industries, Ltd.), 2% B-27®, 1× GlutaMax I (Life Technologies Corp.), 1×NEAA (Life Technologies Corp.), and 100 ng/ml bFGF was added at 5 ml/10-cm dish (a total of 15 ml). Then, half the amount of the medium was replaced with the same medium as above every day for 5 days. On day 9, the whole amount of the medium was replaced with Essential 8 medium. Then, the medium was replaced with the same medium as above every other day. After observation of iPS cell colonies, the cells were appropriately picked up, and the culture was continued to establish iPS cell lines.

Three human iPS cell lines (NTE-1-7, NTE-1-8, and NTE-1-9) thus established were each subjected to the method shown in Reference Example 1 to induce PDX1-positive cells. The cells thus induced were washed with IMEM-option $Zn^{++}$ medium and then further cultured for 7 days using IMEM-option $Zn^{++}$ medium (containing 1% B-27®) supplemented with XAV939 (1 μM) and bFGF (50 ng/ml) to induce PDX1-positive and NKX6.1-positive pancreatic progenitor cells. The cells thus induced were washed with PBS. Then, Accutase was added to the cells, which were then incubated for 4 minutes and then brought to a single cell state by pipetting. The cells were washed with IMEM-option $Zn^{++}$ medium and then inoculated at ¼ to ⅟10 of the cells concentration before passaging to a fresh culture vessel coated with Matrigel. The medium used was IMEM-option $Zn^{++}$ medium containing 1% B-27®, Y27632 (10 μM), XAV939 (1 μM), and bFGF (50 ng/ml). After the passaging, the medium was replaced with a fresh one every day. The cells repetitively passaged two times were subjected to the immunofluorescence staining described in Example 1 and observed under a fluorescence microscope. The results are shown in FIG. 8.

In the case of using any of the cell lines, a great majority of cells after the passaging were PDX1-positive and NKX6.1-positive pancreatic progenitor cells, demonstrating that the method of the present invention is also effective for cell lines other than the 297L1 cells.

(Reference Example 3) Differentiation Induction of Insulin-Producing Cells from Proliferated Pancreatic Progenitor Cells Study was made on whether the proliferated and repetitively passaged pancreatic progenitor cells would have the ability to differentiate into INSULIN-producing cells. The cells used were 297L1 cell-derived pancreatic progenitor cells (passage number: 7). The pancreatic progenitor cells brought to a single cell state using Accutase were inoculated at $6\times10^4$ cells/well to a 96-well plate coated with Matrigel. The culture solution used was IMEM-option $Zn^{++}$ medium (containing 1% B-27®) supplemented with XAV939 (1 µM), Y27632 (10 µM), and bFGF (50 ng/ml). The cells were cultured for 2 days to render the cell density confluent. Then, the cells were washed with IMEM-option $Zn^{++}$ medium and then cultured for 9 days using IMEM-option $Zn^{++}$ medium (containing 1% B-27®) supplemented with ALKS inhibitor II. The ALKS inhibitor II is known to induce INSULIN-positive cells (Stem Cell Research 2012, 8, 274-284). 4% PFA was added to the cells thus cultured, and the cells were fixed at room temperature for 30 minutes. The cells were further reacted with an anti-NKX6.1 antibody and an anti-INSULIN antibody (DAKO, A0564) as primary antibodies and further with an Alexa 488-labeled secondary antibody or an Alexa 568-labeled secondary antibody as a secondary antibody, sequentially, and then observed under a fluorescence microscope. The results are shown in FIG. 9. The manner in which INSULIN-positive cells appeared by culture in a medium supplemented with ALKS inhibitor II was observed. From these results, the proliferated pancreatic progenitor cells were confirmed to be cells having the ability to differentiate into INSULIN-positive cells.

INDUSTRIAL APPLICABILITY

The present invention can proliferate pancreatic progenitor cells at high efficiency and high purity with their functions maintained. The method of the present invention can be applied to living body-derived pancreatic progenitor cells as well as pancreatic progenitor cells differentiation-induced from pluripotent stem cells such as ES cells and iPS cells. The obtained pancreatic progenitor cells are highly functional, highly pure, and highly safe. Thus, the pancreatic progenitor cells can be used, either directly or after being induced to differentiate into pancreatic β cells or the like, in the treatment of diabetes mellitus, a testing method for a therapeutic drug for diabetes mellitus, etc.

All publications, patents, and patent applications cited herein are incorporated herein by reference in their entirety.

The invention claimed is:

1. A method for proliferation of pancreatic progenitor cells, comprising:
   culturing the pancreatic progenitor cells in a medium comprising (i) an EGF signal transduction activator and/or an FGF signal transduction activator, and (ii) a Wnt signal inhibitor, wherein the Wnt signal inhibitor is selected from the group consisting of IWP2, IWP3, IWP4, 2-(4-trifluoromethylphenyl)-7,8-dihydro-5H-thiopyrano[4,3-d]pyrimidin-4(3H)-one (XAV939), IWR1, G-CSF, IGFBP4, Dkk1, and Frzb-1.

2. The proliferation method according to claim 1, wherein the pancreatic progenitor cells are pancreatic progenitor cells induced by culturing PDX1-positive cells in a medium comprising (a) the EGF signal transduction activator and/or the FGF signal transduction activator and (b) the Wnt signal inhibitor.

3. The proliferation method according to claim 1, wherein the EGF signal transduction activator is selected from the group consisting of EGF, TGFalpha, HB-EGF, Amphiregulin, Betacellulin, and Epiregulin, and wherein the FGF signal transduction activator is selected from the group consisting of aFGF (FGF1), bFGF (FGF2), and any one of FGF3 to FGF23.

4. The proliferation method according to claim 1, wherein the medium further comprises (iii) a ROCK inhibitor.

5. The proliferation method according to claim 4, wherein the ROCK inhibitor is selected from the group consisting of N-(4-pyridinyl)-4β-[(R)-1-aminoethyl]cyclohexane-1α-carboxamide (Y-27632), Fasudil (HA1077), (2S)-2-methyl-1-[(4-methyl-5-isoquinolinyl)sulfonyl]hexahydro-1H-1,4-diazepine (H-1152), 4β-[(1R)-1-aminoethyl]-N-(4-pyridyl)benzene-1α-carboxamide (Wf-536), N-(1H-pyrrolo[2,3-b]pyridin-4-yl)-4PER(R)-1-aminoethyl]cyclohexane-1α-carboxamide (Y-30141), N-(3-{[2-(4-amino-1,2,5-oxadiazol-3-yl)-1-ethyl-1H-imidazo[4,5-c]pyridin-6-yl]oxy}phenyl)-4-{[2-(4-morpholinyl)ethyl]-oxy}benzamide (GSK269962A), and N-(6-fluoro-1H-imidazol-5-yl)-6-methyl-2-oxo-4-[4-(trifluoromethyl)phenyl]-3,4-dihydro-1H-pyridine-5-carboxamide (GSK429286A).

6. A method for production of pancreatic progenitor cells, comprising:
   culturing and proliferating pancreatic progenitor cells in a medium comprising (i) an EGF signal transduction activator and/or an FGF signal transduction activator, and (ii) a Wnt signal inhibitor, wherein the Wnt signal inhibitor is selected from the group consisting of IWP2, IWP3, IWP4, 2-(4-trifluoromethylphenyl)-7,8-dihydro-5H-thiopyrano[4,3-d]pyrimidin-4(3H)-one (XAV939), IWR1, G-CSF, IGFBP4, Dkk1, and Frzb-1; and
   collecting the pancreatic progenitor cells from the cultures.

7. The production method according to claim 6, further comprising culturing PDX1-positive cells in a medium comprising (a) the EGF signal transduction activator and/or the FGF signal transduction activator and (b) the Wnt signal inhibitor to induce differentiation thereof into the pancreatic progenitor cells.

8. The production method according to claim 6, wherein the EGF signal transduction activator is selected from the group consisting of EGF, TGFalpha, HB-EGF, Amphiregulin, Betacellulin, and Epiregulin, and wherein the FGF signal transduction activator is selected from the group consisting of aFGF (FGF1), bFGF (FGF2), and any one of FGF3 to FGF23.

* * * * *